US007954191B2

(12) United States Patent
Hohlbein

(10) Patent No.: US 7,954,191 B2
(45) Date of Patent: **\*Jun. 7, 2011**

(54) TOOTHBRUSH

(75) Inventor: Douglas Hohlbein, Pennington, NJ (US)

(73) Assignee: Colgate-Palmolive Company, New York, NY (US)

( \* ) Notice: Subject to any disclaimer, the term of this patent is extended or adjusted under 35 U.S.C. 154(b) by 0 days.

This patent is subject to a terminal disclaimer.

(21) Appl. No.: 11/733,190

(22) Filed: Apr. 9, 2007

(65) Prior Publication Data

US 2007/0186364 A1 Aug. 16, 2007

Related U.S. Application Data

(63) Continuation of application No. 11/089,746, filed on Mar. 25, 2005, now Pat. No. 7,213,288, which is a continuation of application No. PCT/US03/30633, filed on Sep. 26, 2003.

(60) Provisional application No. 60/414,117, filed on Sep. 27, 2002.

(51) Int. Cl.
*A46B 13/02* (2006.01)
*A46B 9/04* (2006.01)

(52) U.S. Cl. ............... 15/22.1; 15/28; 15/167.1; 15/110

(58) Field of Classification Search .................... 15/22.2, 15/22.1, 110, 167.1, 28, 207.2, DIG. 5; D4/104, D4/107, 132, 134
See application file for complete search history.

(56) References Cited

U.S. PATENT DOCUMENTS

| 411,910 A | 10/1889 | Van Home |
| 585,358 A | 6/1897 | Gould |
| 697,336 A | 4/1902 | Hagerty |
| 726,727 A | 4/1903 | Mills |
| 864,054 A | 8/1907 | Abrams |
| 907,842 A | 12/1908 | Meuzies |
| 1,002,468 A | 9/1911 | Strangman |
| 1,006,630 A | 10/1911 | Clarke |
| 1,125,532 A | 1/1915 | Himmel |
| 1,128,139 A | 2/1915 | Hoffman |
| 1,142,698 A | 6/1915 | Grove et al. |
| 1,153,409 A | 9/1915 | Wheeler |
| 1,188,823 A | 6/1916 | Plank |

(Continued)

FOREIGN PATENT DOCUMENTS

CH 99738 6/1923

(Continued)

OTHER PUBLICATIONS

Abstract of Japanese patent application publication 2000-000118 published Jan. 2000.*

(Continued)

*Primary Examiner* — Gary K Graham
(74) *Attorney, Agent, or Firm* — Judy W. Chung

(57) ABSTRACT

A toothbrush includes a head having a prophylaxis polishing cup closely surrounded by cleaning elements in the form of a bristle ring extending above the upper surface of the cup. Alternatively, the cups could be in the form of arrays of densely packed cleaning elements. The area formed by these configurations retains toothpaste on the toothbrush during use. Additional cleaning elements may be arranged about the periphery of the toothbrush head. The toothbrush may be a powered toothbrush wherein the cups and/or bristle rings rotate, oscillate or reciprocate to better clean teeth.

19 Claims, 3 Drawing Sheets

U.S. PATENT DOCUMENTS

| | | |
|---|---|---|
| 1,191,556 A | 7/1916 | Blake |
| 1,251,250 A | 12/1917 | Libby |
| 1,268,544 A | 6/1918 | Cates |
| 1,297,272 A | 3/1919 | Strang et al. |
| 1,405,279 A | 1/1922 | Cassedy |
| 1,470,710 A | 10/1923 | Davis |
| 1,495,675 A | 5/1924 | Colt |
| 1,526,267 A | 2/1926 | Dessau |
| 1,576,074 A | 3/1926 | Chandler |
| 1,588,785 A | 6/1926 | Van Sant |
| 1,598,224 A | 8/1926 | Van Sant |
| 1,658,706 A | 2/1928 | Carrott |
| 1,704,564 A | 3/1929 | Friedland |
| 1,705,109 A | 3/1929 | Essbach |
| 1,728,956 A | 9/1929 | Damitzel |
| 1,741,143 A | 12/1929 | Chin |
| 1,816,582 A | 7/1931 | Heron |
| 1,817,585 A | 8/1931 | Samuel |
| 1,852,480 A | 4/1932 | Ruelz |
| 1,860,924 A | 5/1932 | Cooke |
| 1,861,347 A | 5/1932 | Johnson |
| 1,872,832 A | 6/1932 | Silverberg |
| 1,891,864 A | 12/1932 | Barrett |
| 1,892,068 A | 12/1932 | Metzler |
| 1,903,161 A | 3/1933 | Barkan |
| 1,910,414 A | 5/1933 | Varga |
| 1,924,152 A | 6/1933 | Coney et al. |
| 1,993,662 A | 3/1935 | Green |
| 1,993,763 A | 3/1935 | Touchstone |
| D099,352 S | 4/1936 | Grapp |
| 2,042,239 A | 5/1936 | Planding |
| 2,049,956 A | 8/1936 | Greenberg |
| 2,059,914 A | 11/1936 | Rosenberg |
| 2,079,728 A | 5/1937 | Arnold |
| 2,083,217 A | 6/1937 | Brothers et al. |
| 2,088,839 A | 8/1937 | Coney et al. |
| 2,117,174 A | 5/1938 | Jones |
| 2,139,245 A | 12/1938 | Ogden |
| 2,140,307 A | 12/1938 | Belaschk et al. |
| 2,154,846 A | 4/1939 | Heymann et al. |
| 2,161,349 A | 6/1939 | Hadden |
| 2,186,005 A | 1/1940 | Casto |
| D122,815 S | 10/1940 | Crosby |
| 2,218,072 A | 10/1940 | Runnels |
| 2,219,753 A | 10/1940 | Sequin |
| 2,225,331 A | 12/1940 | Campbell |
| 2,233,936 A | 3/1941 | Campbell |
| 2,244,699 A | 6/1941 | Hosey |
| 2,253,210 A | 8/1941 | Psiharis |
| 2,253,910 A | 8/1941 | Luenz |
| 2,263,802 A | 11/1941 | Grusin |
| 2,279,355 A | 4/1942 | Wilensky |
| 2,305,461 A | 12/1942 | Spyra |
| 2,312,826 A | 3/1943 | Adamsson |
| 2,312,828 A | 3/1943 | Adamsson |
| 2,364,205 A | 12/1944 | Fuller |
| 2,405,029 A | 7/1946 | Gallanty et al. |
| 2,418,485 A | 4/1947 | Shipley |
| 2,443,461 A | 6/1948 | Kempster |
| 2,491,274 A | 12/1949 | McNeill |
| 2,512,059 A | 6/1950 | Haeusser |
| 2,651,068 A | 11/1950 | Seko |
| 2,543,999 A | 3/1951 | Voss |
| 2,545,814 A | 3/1951 | Kempster |
| D162,941 S | 4/1951 | Ehrman |
| 2,554,777 A | 5/1951 | Dangin |
| 2,574,654 A | 11/1951 | Moore |
| 2,583,750 A | 1/1952 | Runnels |
| 2,637,870 A | 5/1953 | Cohen |
| 2,642,604 A | 6/1953 | Ferrari |
| 2,708,762 A | 6/1953 | Kling et al. |
| 2,686,325 A | 8/1954 | Silver |
| 2,702,914 A | 3/1955 | Kittle et al. |
| 3,103,027 A | 9/1963 | Birch |
| 3,103,680 A | 9/1963 | Krichmar |
| 3,153,800 A | 10/1964 | Trotin |
| 3,181,193 A | 5/1965 | Nobles et al. |
| 3,195,537 A | 7/1965 | Blasi |
| 3,230,562 A | 1/1966 | Birch |
| 3,254,356 A | 6/1966 | Yao et al. |
| 3,258,805 A | 7/1966 | Rossnan |
| 3,261,354 A | 7/1966 | Shpuntoff |
| 3,315,296 A | 4/1967 | Richardson |
| 3,337,893 A | 8/1967 | Fine et al. |
| 3,359,688 A | 12/1967 | Kobler |
| 3,491,396 A | 1/1970 | Eannarino at al. |
| 3,509,874 A | 5/1970 | Stillman |
| 3,553,759 A | 1/1971 | Kramer et al. |
| 3,610,043 A | 10/1971 | Wemyss |
| 3,633,237 A | 1/1972 | Bagube |
| 3,638,270 A | 2/1972 | Schlegel, Jr. et al. |
| 3,939,522 A | 2/1976 | Shimizu |
| 4,128,910 A | 12/1978 | Nakata et al. |
| 4,249,521 A | 2/1981 | Gueret |
| 4,277,862 A | 7/1981 | Weideman |
| 4,292,705 A | 10/1981 | Stouffer |
| 4,299,208 A | 11/1981 | Bianc |
| 4,328,604 A | 5/1982 | Adams |
| 4,356,585 A | 11/1982 | Protell et al. |
| 4,364,142 A | 12/1982 | Pangle |
| D272,683 S | 2/1984 | Stocchi |
| D272,687 S | 2/1984 | Stocchi |
| D272,689 S | 2/1984 | Stocchi |
| D272,690 S | 2/1984 | Stocchi |
| D273,635 S | 5/1984 | Stocchi |
| 4,455,704 A | 6/1984 | Williams |
| 4,461,285 A | 7/1984 | Courtin |
| 4,486,109 A | 12/1984 | Rosofsky |
| 4,488,327 A | 12/1984 | Snider |
| 4,493,125 A | 1/1985 | Collis |
| 4,573,920 A | 3/1986 | d'Argambeau |
| 4,592,108 A | 6/1986 | Svendsen |
| 4,607,411 A | 8/1986 | Lewis, Jr. |
| 4,610,043 A | 9/1986 | Vezjak |
| 4,628,564 A | 12/1986 | Youssef |
| D295,695 S | 5/1988 | Golzari |
| 4,827,551 A | 5/1989 | Maser et al. |
| 4,827,557 A | 5/1989 | Siler, Jr. et al. |
| 4,888,844 A | 12/1989 | Maggs |
| D309,528 S | 7/1990 | Valenti |
| 5,005,246 A | 4/1991 | Yen-Hul |
| 5,027,796 A | 7/1991 | Linzey |
| 5,032,082 A | 7/1991 | Herrera |
| 5,040,260 A | 8/1991 | Michaels |
| 5,120,225 A | 6/1992 | Amit |
| 5,165,761 A | 11/1992 | Dirksing |
| 5,170,525 A | 12/1992 | Cafaro |
| 5,176,427 A | 1/1993 | Weihrauch |
| 5,211,494 A | 5/1993 | Baijnath |
| 5,226,197 A | 7/1993 | Nack et al. |
| 5,230,118 A | 7/1993 | Chamma |
| 5,242,235 A | 9/1993 | Li |
| 5,249,327 A | 10/1993 | Hing |
| D340,808 S | 11/1993 | Sherman et al. |
| 5,273,425 A | 12/1993 | Hoagland |
| D345,256 S | 3/1994 | Khin |
| 5,305,489 A | 4/1994 | Lage |
| 5,313,909 A | 5/1994 | Tseng et al. |
| 5,335,389 A | 8/1994 | Curtis et al. |
| 5,341,537 A | 8/1994 | Curtis et al. |
| 5,353,460 A | 10/1994 | Bauman |
| 5,373,600 A | 12/1994 | Stojanovski et al. |
| 5,392,483 A | 2/1995 | Heinzelman et al. |
| 5,396,678 A | 3/1995 | Bredall et al. |
| 5,398,369 A | 3/1995 | Heinzelman et al. |
| 5,438,726 A | 8/1995 | Leite |
| 5,445,825 A | 8/1995 | Copelan et al. |
| 5,446,940 A | 9/1995 | Curtis et al. |
| 5,467,495 A * | 11/1995 | Boland et al. .............. 15/28 |
| 5,511,273 A | 4/1996 | Carroll |
| D371,680 S | 7/1996 | Juhlin et al. |
| 5,530,981 A | 7/1996 | Chen |
| 5,535,474 A | 7/1996 | Salazar |
| 5,570,487 A | 11/1996 | Schneider |
| D376,695 S | 12/1996 | Tveras |
| 5,584,690 A | 12/1996 | Maassarani |
| 5,604,951 A | 2/1997 | Shipp |

| | | | | | |
|---|---|---|---|---|---|
| 5,613,262 A | 3/1997 | Choy-Maldonado | D425,306 S | 5/2000 | Beals et al. |
| 5,625,916 A | 5/1997 | McDougall | 6,058,541 A | 5/2000 | Masterman et al. |
| 5,628,082 A | 5/1997 | Moskovich | 6,065,176 A | 5/2000 | Watanabe et al. |
| D386,905 S | 12/1997 | Brady et al. | 6,067,684 A | 5/2000 | Kweon |
| 5,709,004 A | 1/1998 | Paduano et al. | D427,437 S | 7/2000 | Vonarburg |
| D391,769 S | 3/1998 | Kling et al. | 6,098,233 A | 8/2000 | Chen |
| 5,729,858 A | 3/1998 | Riffel | 6,105,191 A | 8/2000 | Chen et al. |
| 5,735,011 A | 4/1998 | Asher | 6,108,851 A | 8/2000 | Bredall et al. |
| 5,735,012 A | 4/1998 | Heinzelman et al. | 6,108,869 A | 8/2000 | Meessmann et al. |
| 5,735,864 A | 4/1998 | Heisinger, Jr. | 6,119,296 A | 9/2000 | Noe et al. |
| 5,742,972 A | 4/1998 | Bredall et al. | 6,131,228 A | 10/2000 | Chen et al. |
| 5,758,380 A | 6/1998 | Vrignaud | 6,151,745 A | 11/2000 | Roberts et al. |
| 5,766,193 A | 6/1998 | Millner | D434,906 S | 12/2000 | Beals et al. |
| D396,288 S | 7/1998 | Samuel | 6,168,434 B1 | 1/2001 | Bohm-Van Diggelen |
| 5,778,475 A | 7/1998 | Garcia | 6,171,323 B1 | 1/2001 | Potti et al. |
| 5,778,476 A | 7/1998 | Squillaci et al. | 6,182,365 B1 | 2/2001 | Tseng et al. |
| 5,779,654 A | 7/1998 | Foley et al. | D439,412 S | 3/2001 | Volpenhein et al. |
| 5,784,742 A | 7/1998 | Giuliani et al. | D440,767 S | 4/2001 | Moskovich et al. |
| D397,219 S | 8/1998 | Rangel et al. | D440,787 S | 4/2001 | Moskovich et al. |
| 5,792,159 A | 8/1998 | Armin | 6,254,390 B1 | 7/2001 | Wagner |
| 5,799,353 A | 9/1998 | Oishi et al. | 6,260,227 B1 | 7/2001 | Fulop et al. |
| 5,802,656 A | 9/1998 | Dawson et al. | 6,276,021 B1 | 8/2001 | Hohlbein |
| 5,806,127 A | 9/1998 | Samoil et al. | D448,174 S | 9/2001 | Harris et al. |
| 5,809,608 A | 9/1998 | Zadro | 6,289,545 B1 | 9/2001 | Molster |
| 5,810,856 A | 9/1998 | Tveras | D448,569 S | 10/2001 | Harris et al. |
| D399,349 S | 10/1998 | Barth | D450,299 S | 11/2001 | Ma et al. |
| 5,817,114 A | 10/1998 | Anderson et al. | D450,457 S | 11/2001 | Hohlbein |
| 5,818,856 A | 10/1998 | Injeyan et al. | D450,929 S | 11/2001 | Angelini et al. |
| RE35,941 E | 11/1998 | Stansbury, Jr. | 6,311,358 B1 | 11/2001 | Soetewey et al. |
| D402,116 S | 12/1998 | Magloff et al. | 6,319,332 B1 | 11/2001 | Gavney, Jr. et al. |
| 5,842,245 A | 12/1998 | Pai et al. | 6,322,573 B1 | 11/2001 | Murayama |
| 5,842,247 A | 12/1998 | Decesare et al. | D452,615 S | 1/2002 | Cheong et al. |
| 5,845,358 A | 12/1998 | Woloch | D453,270 S | 2/2002 | Choong |
| D403,510 S | 1/1999 | Menke et al. | 6,345,405 B1 | 2/2002 | Brackin |
| 5,860,183 A | 1/1999 | Kam | D453,998 S | 3/2002 | Ping |
| D405,272 S | 2/1999 | Khlaj et al. | D454,252 S | 3/2002 | Lee |
| 5,873,140 A | 2/1999 | Holloway | 6,352,545 B1 | 3/2002 | Wagner |
| 5,875,510 A | 3/1999 | Lamond et al. | 6,353,958 B2 | 3/2002 | Weihrauch |
| 5,896,614 A | 4/1999 | Flewitt | RE37,625 E | 4/2002 | Wieder et al. |
| 5,913,346 A | 6/1999 | Narwani | D456,139 S | 4/2002 | Hohlbein |
| 5,915,433 A | 6/1999 | Hybler | 6,374,448 B2 | 4/2002 | Seifert |
| D412,064 S | 7/1999 | Achepohl et al. | D456,607 S | 5/2002 | Carlucci et al. |
| 5,920,941 A | 7/1999 | Iannotta | D457,323 S | 5/2002 | Hohlbein |
| 5,928,254 A | 7/1999 | Jensen | D457,325 S | 5/2002 | Wilson et al. |
| 5,930,860 A | 8/1999 | Shipp | 6,383,202 B1 | 5/2002 | Rosenblood |
| 5,930,861 A | 8/1999 | White | 6,389,634 B1 | 5/2002 | Devlin et al. |
| 5,938,673 A | 8/1999 | DePierro et al. | D458,453 S | 6/2002 | Baertschi |
| D413,728 S | 9/1999 | Waguespack et al. | D459,086 S | 6/2002 | Belton et al. |
| 5,946,759 A | 9/1999 | Cann | 6,402,768 B1 | 6/2002 | Liebel |
| 5,951,578 A | 9/1999 | Jensen | 6,408,476 B1 | 6/2002 | Cann |
| 5,957,942 A | 9/1999 | Yudelman | 6,421,867 B1 | 7/2002 | Weihrauch |
| 5,967,152 A | 10/1999 | Rimkus | D461,313 S | 8/2002 | Hohlbein |
| 5,970,564 A | 10/1999 | Inns et al. | D461,959 S | 8/2002 | Chan et al. |
| D416,685 S | 11/1999 | Overthun | D462,178 S | 9/2002 | Moskovich et al. |
| 5,974,614 A | 11/1999 | Ross | D462,528 S | 9/2002 | Crossman et al. |
| 5,980,541 A | 11/1999 | Tenzer | D463,132 S | 9/2002 | Winter et al. |
| 5,980,542 A | 11/1999 | Saldivar | D463,133 S | 9/2002 | Hohlbein |
| 5,984,935 A | 11/1999 | Welt et al. | 6,442,785 B1 | 9/2002 | Robinson |
| 5,991,959 A | 11/1999 | Raven et al. | 6,446,295 B1 | 9/2002 | Calabrese |
| D418,979 S | 1/2000 | Moskovich et al. | D463,668 S | 10/2002 | Yoshimoto et al. |
| D418,981 S | 1/2000 | Cheong et al. | 6,463,618 B1 | 10/2002 | Zimmer |
| D419,304 S | 1/2000 | Moskovich et al. | 6,463,619 B2 | 10/2002 | Gavney, Jr. |
| 6,015,293 A | 1/2000 | Rimkus | D465,847 S | 11/2002 | Jacobs |
| D419,773 S | 2/2000 | Beals et al. | D465,927 S | 11/2002 | Saindon et al. |
| D420,802 S | 2/2000 | Cheong et al. | D466,302 S | 12/2002 | Ping |
| D420,804 S | 2/2000 | Juhlin et al. | D466,303 S | 12/2002 | Saindon et al. |
| 6,029,304 A | 2/2000 | Hulke et al. | D466,694 S | 12/2002 | Saindon et al. |
| D421,841 S | 3/2000 | Achepohl et al. | 6,496,999 B1 | 12/2002 | Gleason et al. |
| 6,032,315 A | 3/2000 | Liebel | 6,510,575 B2 | 1/2003 | Calabrese et al. |
| 6,041,467 A | 3/2000 | Roberts et al. | D469,958 S | 2/2003 | Saindon et al. |
| 6,041,468 A | 3/2000 | Chen et al. | 6,513,182 B1 | 2/2003 | Calabrese et al. |
| D422,143 S | 4/2000 | Beals et al. | D471,276 S | 3/2003 | Potti |
| D422,413 S | 4/2000 | Goldinger et al. | D471,362 S | 3/2003 | Moskovich et al. |
| 6,044,514 A | 4/2000 | Kaneda et al. | 6,546,586 B2 | 4/2003 | Cho |
| D423,785 S | 5/2000 | Karallis | D474,608 S | 5/2003 | Hohlbein |
| D423,786 S | 5/2000 | Zelinski | D475,531 S | 6/2003 | Kilmeck et al. |
| D423,787 S | 5/2000 | Musciano | D476,158 S | 6/2003 | Ling |
| D424,808 S | 5/2000 | Beals et al. | D476,424 S | 6/2003 | Shanahan |
| D424,809 S | 5/2000 | Bernard | 6,571,417 B1 | 6/2003 | Gavney, Jr. |

| | | | | | | |
|---|---|---|---|---|---|---|
| D478,213 S | 8/2003 | Ping | | DE | 31 14 507 | 3/1983 |
| D478,424 S | 8/2003 | Saindon et al. | | DE | 3114507 | 3/1983 |
| D478,425 S | 8/2003 | Ping | | DE | 3428860 * | 2/1986 |
| D478,727 S | 8/2003 | Wong | | DE | 3639424 | 6/1988 |
| D479,046 S | 9/2003 | Winkler | | EP | 360 766 | 3/1990 |
| D479,047 S | 9/2003 | Wong | | EP | 0449655 | 5/1995 |
| D479,914 S | 9/2003 | Choong | | EP | 0875169 | 4/1998 |
| 6,625,839 B2 | 9/2003 | Fischer | | EP | 1034721 | 9/2000 |
| D480,213 S | 10/2003 | Ping | | EP | 1 308 108 | 5/2003 |
| D480,562 S | 10/2003 | Saindon et al. | | EP | 1308108 | 5/2003 |
| D482,199 S | 11/2003 | De Salvo | | EP | 1425989 | 6/2004 |
| 6,643,886 B2 | 11/2003 | Moskovich et al. | | FR | 537979 | 6/1922 |
| 6,647,581 B1 | 11/2003 | Persad et al. | | FR | 2594307 | 4/1987 |
| D483,183 S | 12/2003 | De Salvo | | FR | 2636818 | 9/1988 |
| D483,184 S | 12/2003 | Geiberger et al. | | FR | 2793136 | 5/1999 |
| D483,568 S | 12/2003 | Jamson | | GB | 17643 | 4/1912 |
| 6,654,979 B2 | 12/2003 | Calabrese | | GB | 388246 | 2/1933 |
| 6,658,688 B2 | 12/2003 | Gavney, Jr. | | GB | 495982 | 11/1938 |
| 6,665,901 B2 | 12/2003 | Driesen et al. | | GB | 2040161 | 1/1979 |
| D486,649 S | 2/2004 | Sprosta et al. | | GB | 2371217 | 7/2002 |
| 6,687,940 B1 | 2/2004 | Gross et al. | | GB | 2391462 | 2/2004 |
| D487,195 S | 3/2004 | Winkler | | GB | 2375705 | 1/2005 |
| 6,729,789 B2 | 5/2004 | Gordon | | JP | 51 35303 | 8/1976 |
| 6,735,804 B2 | 5/2004 | Carlucci et al. | | JP | 6-14709 | 1/1994 |
| 6,817,054 B2 | 11/2004 | Moskovich et al. | | JP | 9-182626 | 7/1997 |
| 6,859,969 B2 | 3/2005 | Gavney et al. | | JP | 10-42957 | 2/1998 |
| D503,538 S | 4/2005 | De Salvo | | JP | 2000-000118 * | 1/2000 |
| 6,886,207 B1 | 5/2005 | Solanki | | JP | 2000-278899 | 10/2000 |
| 6,895,629 B1 | 5/2005 | Wenzler | | JP | 2000-308522 | 11/2000 |
| 7,089,621 B2 * | 8/2006 | Hohlbein ......... 15/110 | | JP | 2000308522 | 11/2000 |
| 7,213,288 B2 * | 5/2007 | Hohlbein ......... 15/22.1 | | JP | 2001-314232 | 11/2001 |
| 7,428,766 B2 * | 9/2008 | Eliav et al. ....... 15/22.1 | | JP | 2002-142867 | 5/2002 |
| 2001/0014232 A1 | 8/2001 | Ichimura | | SU | 1708283 | 1/1992 |
| 2001/0023516 A1 | 9/2001 | Driesen et al. | | WO | WO 96/01578 | 1/1996 |
| 2001/0041903 A1 | 11/2001 | Richard | | WO | WO 96/15696 | 5/1996 |
| 2001/0042280 A1 | 11/2001 | Moskovich et al. | | WO | WO 96/28994 | 9/1996 |
| 2002/0004964 A1 | 1/2002 | Luchino et al. | | WO | 97/04686 * | 2/1997 |
| 2002/0019645 A1 | 2/2002 | Fischer et al. | | WO | WO 97/03587 | 2/1997 |
| 2002/0029988 A1 | 3/2002 | Blaustein et al. | | WO | 97/25898 * | 7/1997 |
| 2002/0032941 A1 * | 3/2002 | Blaustein et al. ...... 15/22.1 | | WO | WO 98/05241 | 2/1998 |
| 2002/0059685 A1 | 5/2002 | Paffrath | | WO | WO 98/08458 | 3/1998 |
| 2002/0095734 A1 * | 7/2002 | Wong ................ 15/22.1 | | WO | WO 98/09573 | 3/1998 |
| 2002/0108194 A1 | 8/2002 | Carlucci et al. | | WO | WO 98/18364 | 5/1998 |
| 2002/0124333 A1 | 9/2002 | Hafliger et al. | | WO | WO 98/22000 | 5/1998 |
| 2002/0124337 A1 | 9/2002 | Calabrese et al. | | WO | WO 99/01054 | 1/1999 |
| 2002/0138926 A1 | 10/2002 | Brown, Jr. et al. | | WO | WO 99/07251 | 2/1999 |
| 2002/0138928 A1 | 10/2002 | Calabrese | | WO | 9945819 A | 9/1999 |
| 2002/0152584 A1 | 10/2002 | Blaustein et al. | | WO | WO 99/37182 | 9/1999 |
| 2002/0162180 A1 | 11/2002 | Blaustein et al. | | WO | WO 99/49754 | 10/1999 |
| 2003/0009837 A1 | 1/2003 | Cann | | WO | WO 00/53054 | 9/2000 |
| 2003/0026738 A1 | 2/2003 | Everett | | WO | WO 00/64307 | 11/2000 |
| 2003/0033680 A1 | 2/2003 | Davies et al. | | WO | WO 01/01817 | 1/2001 |
| 2003/0033682 A1 | 2/2003 | Davies et al. | | WO | WO 01/17433 | 3/2001 |
| 2003/0115699 A1 | 6/2003 | Wagstaff | | WO | WO 01/45573 | 6/2001 |
| 2003/0116884 A1 | 6/2003 | Wagstaff | | WO | WO 01/80686 | 11/2001 |
| 2003/0163149 A1 | 8/2003 | Heisinger, Jr. | | WO | 02/45617 * | 6/2002 |
| 2003/0167582 A1 | 9/2003 | Fischer et al. | | WO | WO 02/062174 | 8/2002 |
| 2003/0192139 A1 | 10/2003 | Fattori et al. | | WO | WO 02/071967 | 9/2002 |
| 2003/0196283 A1 | 10/2003 | Gatzemeyer et al. | | WO | WO 03/030680 | 4/2003 |
| 2003/0208865 A1 | 11/2003 | Davies | | WO | WO 2004/019801 | 3/2004 |
| 2003/0216762 A1 | 11/2003 | Levit | | WO | WO 2004/026162 | 4/2004 |
| 2003/0229959 A1 | 12/2003 | Kim et al. | | WO | WO 2004/028235 | 4/2004 |
| 2004/0006837 A1 | 1/2004 | Cann | | WO | WO 2006/044964 | 4/2006 |
| 2004/0025275 A1 | 2/2004 | Moskovich et al. | | | | |
| 2004/0068810 A1 | 4/2004 | Lee | | | | |
| 2004/0134007 A1 | 7/2004 | Davies | | | | |
| 2004/0200748 A1 | 10/2004 | Klassen et al. | | | | |
| 2004/0255416 A1 | 12/2004 | Hohlbein | | | | |
| 2005/0000049 A1 | 1/2005 | Hohlbein | | | | |
| 2005/0069372 A1 | 3/2005 | Hohlbein et al. | | | | |
| 2006/0057087 A1 | 3/2006 | Moskovich et al. | | | | |

FOREIGN PATENT DOCUMENTS

| | | |
|---|---|---|
| CN | 992257042 | 11/1999 |
| DE | 857128 | 11/1952 |
| DE | 2930459 | 2/1981 |

OTHER PUBLICATIONS

European Search Report dated Mar. 11, 2008.
Top and Side Photographs of Head of Reach Max Tooth and Gum Toothbrush.
Sample of Reach Max Tooth and Gum Toothbrush.
Office Action from the Patent Office of China for corresponding Chinese Patent Application No. 03825340.2 dated Sep. 14, 2007.
Office Action from the Patent Office of Russia for corresponding Russian Patent Application No. 2005112732/12.

* cited by examiner

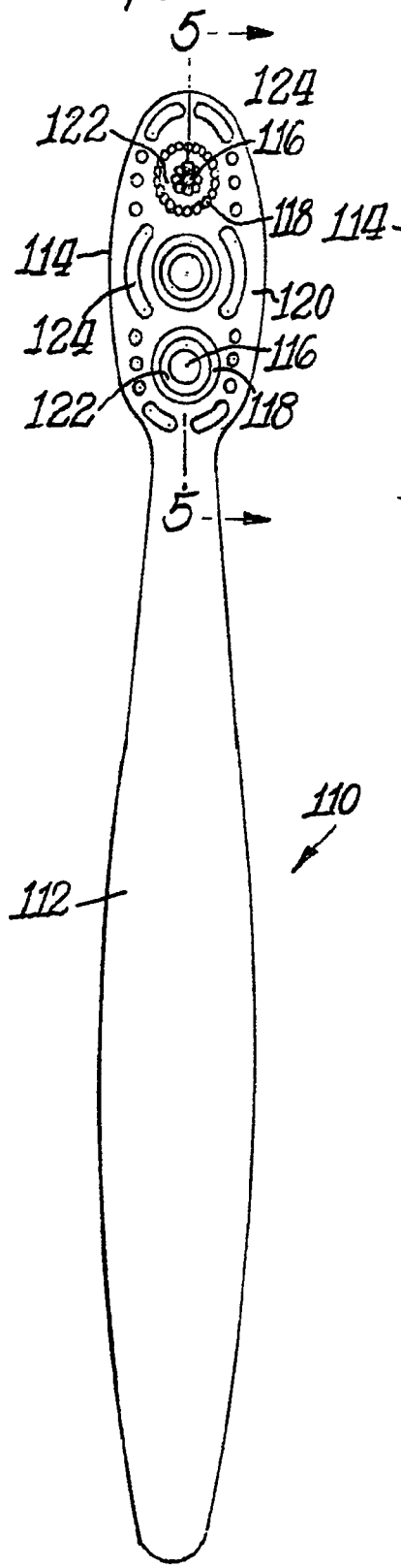
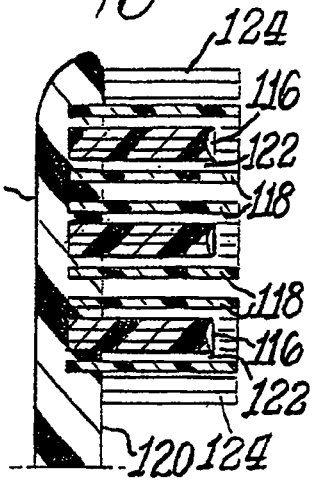
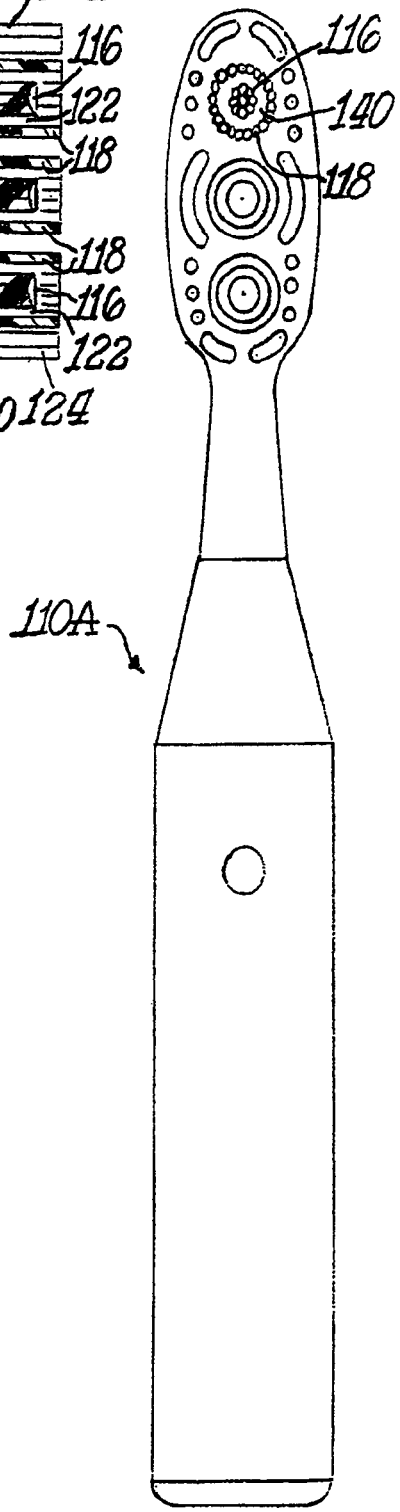

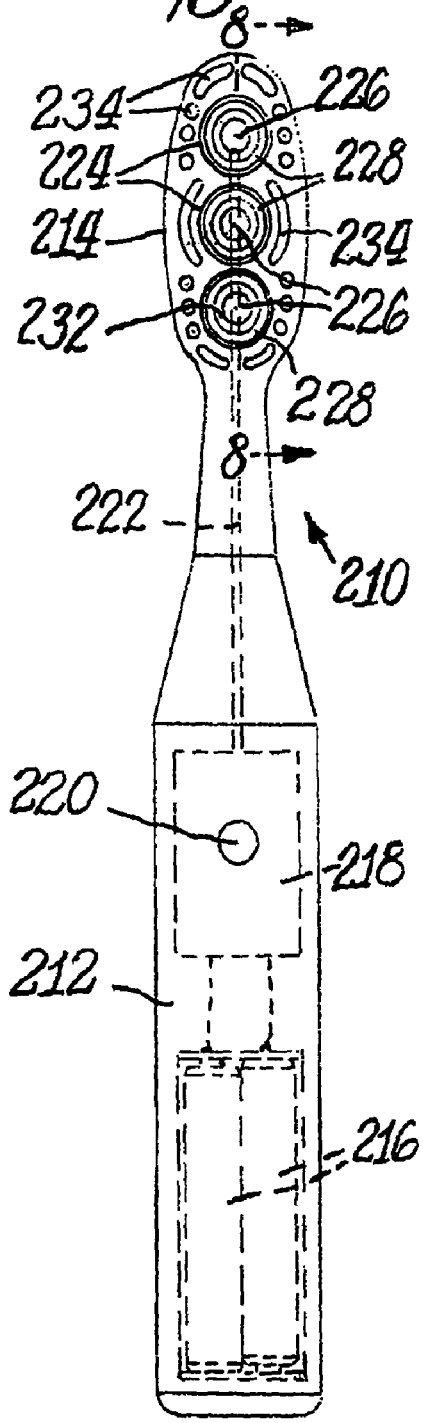
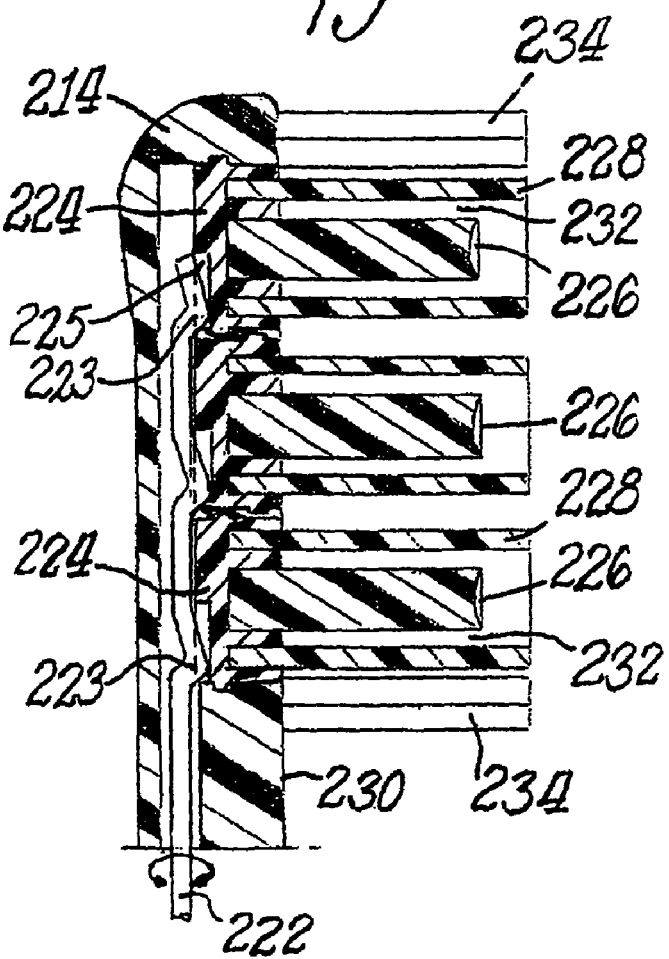

TOOTHBRUSH

This application is a continuation of U.S. patent application Ser. No. 11/089,746 filed Mar. 25, 2005 now U.S. Pat. No. 7,213,288, which is a continuation of the International Application No. PCT/US2003/30633, filed Sep. 26, 2003, (designating the United States of America) which claims the benefit of priority of U.S. Provisional Application No. 60/414,117 filed Sep. 27, 2002, the contents of said applications are hereby incorporated by reference in their entirety.

FIELD OF INVENTION

The present invention is directed to a toothbrush, either manual or powered, which includes a handle and a head. Cleaning elements are mounted to the head such as tufts of bristles. When toothpaste is applied to the cleaning elements the user inserts the head into the mouth and brushes the teeth in a known manner. Also included in this invention are prophylaxis polishing cups or arrays of bristles forming cups in the center of the head to hold toothpaste. These cups are closely surrounded by cleaning elements which help to retain the toothpaste within the head.

BACKGROUND OF THE INVENTION

The head of a conventional toothbrush usually has a flat or slightly altered surface to which cleaning elements are attached. Usually the cleaning elements are strands of plastic material(s) formed into tufts, bundles or other groupings. The strands are attached to the head either before or after forming the toothbrush.

Various approaches have been advanced in the prior art for orientating the cleaning elements in the toothbrush.

U.S. Pat. No. 2,083,217 issued Jun. 8, 1937 to E. I. Brothers, et al. discloses two or three circular brush sections which are arranged within cups 5 and 5' that may be screwed into mating receptacles in the tooth brush handle so that they can be removed and replaced as needed (page 2, lines 52-70). Each brush section contains stiff cleaning elements and is spaced from the other along the longitudinal axis of the handle at a distance less than the thickness of a tooth so that the brush operates on both the lingual (inside) and facial (outside) surfaces of the teeth (page 2, column 1, line 71 to column 2, line 9).

U.S. Pat. No. 5,604,951 describes a toothbrush with a head containing a flexible, rubber-like prophylaxis polishing cup or "prophy cup" similar to that used by dental personnel to professionally clean teeth. This prophy cup is loaded with toothpaste by the user and applied to the teeth. According to this patent, the "soft rubber-like prophy cup device follows the contours of teeth more effectively than bristles" (column 2, lines 23-26). This patent also discloses a ring of cleaning elements ("bristle tufts") placed about the periphery of the toothbrush head which coact with the prophy cups to clean the user's teeth and gums (column 2, lines 34-47).

Another approach to oral hygiene is described in the toothbrush described in U.S. Pat. No. 6,041,468 issued to the assignee of this application. The cleaning elements (bristles) of this toothbrush are arranged in a concave shape across the width of the toothbrush head (See FIGS. 3-5 and column 4, lines 1-22).

Design Patents illustrating circular groups of cleaning elements are U.S. Pat. Nos. Des. 273,635 issued May 1, 1984 to Stocchi and D450,929S issued Nov. 27, 2001 to Angelina, et al.

SUMMARY OF THE INVENTION

This invention seeks to improve the tooth buffing/polishing capability of a toothbrush by inter alia providing a configuration that promotes retention of toothpaste in place within a toothbrush head while in use. This goal is achieved by mounting elastomeric prophy cups on a toothbrush head, which cups are closely surrounded by cleaning elements extending above the surface of the cups.

Unlike a professional dentist's office where the dental professional can repeatedly add toothpaste to a prophy cup, a typical domestic toothbrush user applies but one portion of toothpaste to a toothbrush. A substantial portion of the applied toothpaste, and thus its cleaning power, is typically lost after the first few movements of the toothbrush in the user's mouth. It either falls off as the top of the toothbrush head is tilted from horizontal to vertical as it approaches the mouth or is squeezed off as the toothbrush is pressed against the teeth. The toothpaste is of no cleaning value once it leaves contact with the brush and teeth.

Accordingly, this invention provides a unique combination of features to maintain and retain toothpaste on the head of a toothbrush. Prophy cup(s) are arranged in the center of the toothbrush head, preferably on the longitudinal axis of the head. Alternatively, the cups could be in the form of an array of bristles. These cups are closely surrounded by groupings of cleaning elements that have a greater height relative to the face of the toothbrush head than the height of the prophy cup from that face. This grouping of taller cleaning elements at least partially surrounds the prophy cup to form a barrier around the prophy cup that retains toothpaste when the toothbrush is in use.

An additional set of cleaning elements can then be arranged about the periphery of the toothbrush head to clean the teeth with the toothpaste retained by the prophy cup and surrounding cleaning elements. The outer set of cleaning elements also promotes massaging of the gum and removal of plaque at the gum line.

The cleaning elements are typically bristles secured to the toothbrush head by anchor free tufting (AFT) technology.

The invention may be practiced where each set of cup and surrounding cleaning elements is mounted on a disk and the disk is power driven to rotate continuously in the same direction or back and forth in an oscillating movement.

BRIEF DESCRIPTION OF THE DRAWINGS

This invention is capable of use in a broad array of oral hygiene products. The drawings illustrate one use of the invention and are not to be construed as the only embodiment of the invention.

FIG. 4 is a front elevation view of a toothbrush showing a further arrangement in accordance with this invention;

FIG. 5 is a cross sectional view in elevation taken along the line 5-5 of FIG. 4;

FIG. 6 is a front elevation view of a powered toothbrush incorporating the cup and cleaning element arrangement of FIGS. 4-5;

FIG. 7 is a front elevation view of a powered toothbrush in accordance with yet another arrangement of this invention; and FIG. 8 is a cross section view in elevation taken along the line 8-8 of FIG. 7.

DETAILED DESCRIPTION OF THE INVENTION

Figure 1:
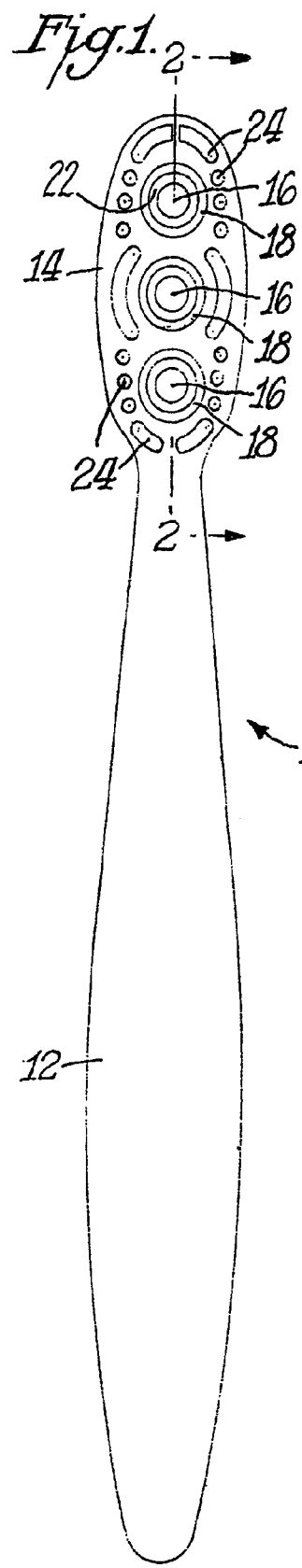
FIG. 1 is a front elevation view of a toothbrush of this invention showing the arrangement of prophy cups and cleaning elements used in this invention.

FIG. 1 illustrates a manual toothbrush 10 containing the features of this invention. This toothbrush 10 includes a handle 12 and a head 14. Handle 12 may include a suitable textured grip (not shown) made of elastomeric material. This invention, however, is primarily directed to the arrangement of prophy cups and cleaning elements on head 14.

In accordance with this invention, prophy cups 16 are arrayed in the center of head 14, preferable aligned with the longitudinal axis of toothbrush 10. As illustrated, three prophy cups 16 are affixed to head 14, although use of a larger or smaller number of such cups is contemplated for use with toothbrush 10. The prophy cups 16 are typically made of a soft elastomeric material and, as the name implies, are cup-shaped. The inner surface of the cup can contain ridges which help to clean teeth when the toothbrush is pressed against the user's teeth. More importantly, the cup shape of prophy cups 16 acts to hold toothpaste in place while the toothbrush 10 is in use.

Figure 2:
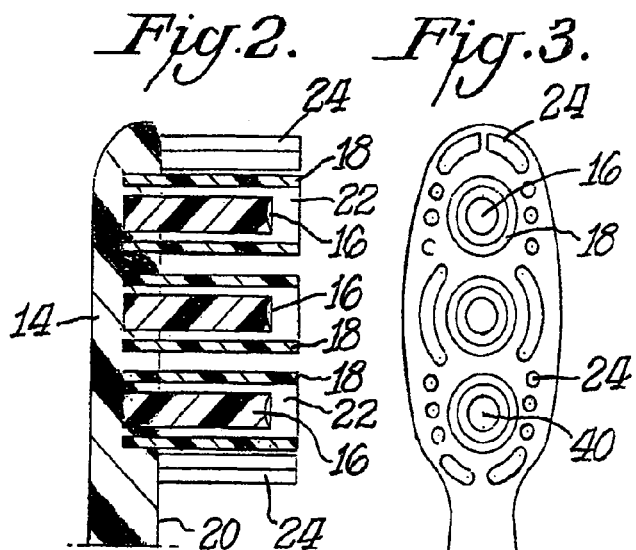
FIG. 2 is a cross-sectional view in elevation taken along the line 2-2 of FIG. 1.

Complementing this function of toothpaste retention is a set of cleaning elements or bristle rings 18 surrounding some or all of the prophy cups 16. As best illustrated in FIG. 2, the bristle rings 18 extend a greater distance above the face 20 of head 14 than the prophy cups 16. This extra height relative to cups 16 acts as a further means for retaining toothpaste within the toothbrush head 14 during use. A preferred placement of the bristle rings 18 is with a space of about one (1) millimeter from the outer circumference of the prophy cup 16.

Upon the user's application of force on the handle 14 as the toothbrush 10 approaches the user's teeth, the toothpaste applied by the user will be forced into the holding areas 22 formed by between a prophy cup 16 and the surrounding bristle ring 18. The toothpaste will be held in holding areas 22 near the top of the bristle rings by the top of prophy cup 16.

This unique combination of prophy cups 16 and closely surrounding bristle rings 18 holds most of the toothpaste exactly where desired, namely, in the area 22 where the principal cleansing components, prophy cup and bristle rings, are in contact with the user's teeth. The surrounding ring of bristles 18 captures the toothpaste as it escapes from the cup 16, to act as a replenishing reservoir when one changes the direction of one's brush stroke.

To complement the cleaning effect of the prophy cups 16 and bristle rings 18, additional elements 24 can be arranged about the periphery of head 14 in a manner similar to that shown in FIGS. 1 and 2. These peripheral cleaning elements 24 help to clean deep between teeth and along the gumline. These additional cleaning elements may be tufts of bristles and may be elastomeric walls or fingers, as illustrated.

Cleaning elements 24 and bristle rings 18 are arranged in both portions of head 14 in a known manner. For example, anchor free tufting (AFT) could be used to mount the cleaning elements. In AFT a plate or membrane is secured to the brush head such as by ultrasonic welding. The bristles extend through the plate or membrane. The free ends of the bristles on one side of the plate or membrane perform the cleaning function. The ends of the bristles on the other side of the plate or membrane are melted together by heat to be anchored in place. Any suitable form of cleaning elements may be used in the broad practice of this invention. The term "cleaning elements" is intended to be used in a generic sense which could include conventional fiber bristles or massage elements or other forms of cleaning elements such as elastomeric fingers or walls arranged in a circular cross-section shape or any type of desired shape including straight portions or sinusoidal portions. Where bristles are used, the bristles could be mounted to tuft blocks or sections by extending through suitable openings in the tuft blocks so that the base of the bristles is mounted within or below the tuft block.

It is to be understood that the specific illustration of the cleaning elements is merely for exemplary purposes. The invention can be practiced with various combinations (such as AFT, etc.) and/or with the same bristle or cleaning element materials (such as nylon bristles, spiral bristles, rubber bristles, etc.) Similarly, while the Figures illustrate the cleaning elements to be generally perpendicular to head 14, some or all of the cleaning elements may be angled at various angles with respect to the face 20 of head 14. It is thereby possible to select the combination of cleaning element configurations, materials and orientations to achieve specific intended results to deliver additional oral health benefits, like enhanced cleaning, tooth polishing, tooth whitening and/or massaging of the gums.

Although the bristle ring 18 is illustrated as being formed by fibrous bristles, the bristle ring could be formed by other types of cleaning elements such as elastomer fingers.

Figure 3:
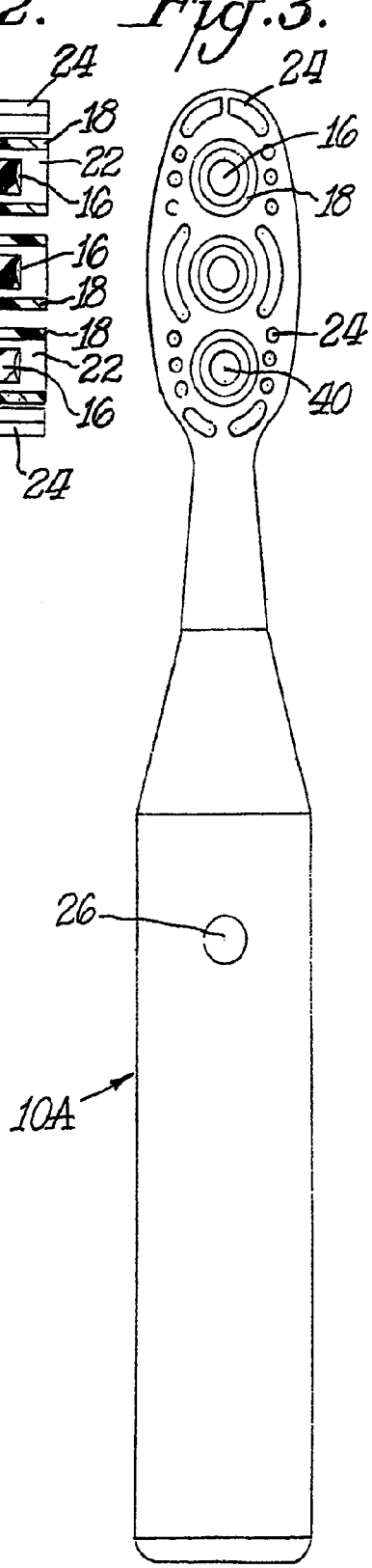
FIG. 3 is a front elevation view of a powered toothbrush in accordance with this invention.

FIG. 3 illustrates a powered version 10A of the toothbrush wherein sections 40 of the head 14 are moved under power or may contain a powered set of cleaning elements. Sections 40 may take the form of circular discs. Preferably, the prophy cups 16 and/or bristle rings 18 would be mounted to the section 40 to be powered to provide rotational or oscillating movement thereto. Switch 26 on toothbrush 10A can be used to activate and deactivate power to the movable elements of toothbrush 10A.

The movable section 40 could be oscillated rotationally such as by using the type of drive mechanism shown in U.S. Pat. No. 5,625,916, or could move in and out using the type of drive mechanism shown in U.S. Pat. No. RE 35,941; all of the details of both patents are incorporated herein by reference thereto. Alternatively, the other types of drives referred to above could move section 40 in other manners and directions. Although FIG. 3 shows movable section 40 to be at one end of the head 14, the movable section(s) would be located at any desired location on the head.

FIGS. 1-3 relate to the practice of the invention wherein the cleaning elements 18 surround prophy cups 16. The invention could, however, be practiced where instead of prophy cups the cups are formed by a dense pack of cleaning elements. This embodiment of the invention is illustrated in FIGS. 4-6. As shown therein the toothbrush 110 has many of the same features as the toothbrush 10. Thus, the toothbrush 110 includes a handle 112 and a head 114 similar to the same components in FIGS. 1-3.

In accordance with the practice of the invention shown in FIGS. 4-6, a central, dense pack of cleaning elements 116 is arrayed in the center of head 114, preferable aligned with the longitudinal axis of toothbrush 110. As illustrated, three circular groups of densely packed cleaning elements 116 are affixed to head 114, although use of a larger or smaller number of such groups is contemplated for use with toothbrush 110. The ends of cleaning element groups 116 are typically contoured in cross-section to provide a cup-like shape. The cup-like shape of cleaning elements 116 acts to hold toothpaste in place while the toothbrush 110 is in use.

Complementing this function of toothpaste retention is a set of cleaning elements or bristle rings 118 surrounding some or all of the cup-shaped cleaning elements 116. As best illustrated in FIG. 5, the bristle rings 118 extend a greater distance above the face 120 of head 114 than the cup-shaped elements 116. This extra height relative to cup-shaped cleaning elements 116 acts as a further means for retaining toothpaste within the toothbrush head 114 during use. A preferred placement of the bristle rings 118 is with a space of about one (1) millimeter from the outer circumference of the cup-shaped elements 116.

Upon the user's application of force on the handle 114 as the toothbrush 110 approaches the user's teeth, the toothpaste applied by the user will be forced into the holding areas 122 formed by the surrounding bristle rings 118. The toothpaste will be held in holding areas 122 near the top of the bristle rings by the top of cup-shaped elements 116.

This unique combination of elements 116 and closely surrounding bristle rings 118 holds most of the toothpaste exactly where desired, namely, in the area 122 adjacent where the principal cleansing components, which are in contact with the user's teeth. The surrounding ring of bristles 118 captures the toothpaste as it escapes from the cup-shaped bristles 116, to act as a replenishing reservoir when one changes the direction of one's brush stroke.

To complement the cleaning effect of the cup-shaped elements 116 and bristle rings 118, additional elements 124 can be arranged about the periphery of head 114 in a manner similar to that shown in FIGS. 4 and 5. These peripheral cleaning elements 124 help to clean deep between teeth and along the gumline.

As with toothbrush 10 of FIGS. 1-2, cleaning elements 116, 118, and 124 are arranged in head 114 in a known manner. Any suitable form of cleaning elements may be used in the broad practice of this invention.

FIG. 6 illustrates a powered version 110A of the toothbrush wherein portions 140 of the head 114 are moved under power or may contain a powered set of cleaning elements. Preferably, the cup-shaped cleaning elements 116 and/or bristle rings 118 would be powered to provide rotational or oscillating movement thereto. A switch 126 on toothbrush 110A can be used to activate and deactivate power to the movable elements of toothbrush 110A. Toothbrush 110A could operate in the same manner as toothbrush 110A.

The toothbrushes 10A and 110A utilize a power drive to move the respective sections 40, 140. FIGS. 7-8 illustrate in greater detail one such practice of the invention. As shown in FIG. 7, a powered toothbrush 210 includes a handle 212 and a head 214. Handle 212 includes a battery pack or rechargeable unit 216 which provides the motive power to toothbrush 210. This power source 216 is electrically connected to motor 218 by suitable wiring or after connection. Selective operation of motor 218 is controlled by switch 220.

Extending from one end of motor 218 toward head 214 is drive shaft 222. Motor 218 can be geared to impart rotational or reciprocating motion to drive shaft 222. The other end underlies the discs or movable platforms 224 on which are mounted cups 226 and taller cleaning elements 228.

In the embodiment illustrated in FIGS. 7 and 8, the drive shaft rotates back and forth through an angle of about 60-90° as illustrated in FIG. 8. Offsets 223 in drive shaft 222 rotate a similar angular distance. These offsets 223 in drive shaft 222 are positioned in slots 225 formed in the base of platforms 224. As the shaft rotates back and forth through the aforesaid angle, offsets 223 cause reciprocation of platforms 224 as the offsets alternatively push the sides of slots 225 in one direction and then another. This, in turn, causes reciprocating movement of cups 226 or bristles 228, depending upon which is mounted on platform 224. That movement aids in cleaning of teeth and invigoration of gums.

In accordance with this invention, cups 226 are mounted on platforms 224 in the center of head 214, preferably aligned with the longitudinal axis of toothbrush 210. As illustrated, three cups 226 are contained in head 214, although use of a larger or smaller number of such cups is contemplated for use with toothbrush 210. Where cups 226 are prophy cups, the prophy cups 226 are typically made of a soft elastomeric material and, as the name implies, are cup-shaped. The inner surface of the cup can contain ridges which help to clean teeth when the toothbrush is pressed against the user's teeth. Also, the cup shape of prophy cups 226 acts to hold toothpaste in place while the powered toothbrush 10 is in use.

Although prophy cups are specifically illustrated, cups 226 could also be densely packed cleaning elements, such as cups 116.

Complementing these functions of toothpaste retention and cleaning is a set of cleaning elements or bristle rings 228 surrounding some or all of the cups 226, as previously described with respect to toothbrushes 10 and 110.

It is to be understood that various features shown in an individual embodiment may be incorporated in other embodiments. Thus, for example, where a toothbrush utilizes a plurality of cups all of the cups may be prophy cups or all of the cups may be cups formed by densely packed cleaning elements. Alternatively, a combination of the two different types of cups may be used in any suitable arrangement. Thus, where three cups are used the end cups may be of one type which differs from the central cup or only one of the end cups may differ from the other cups. Where more than three cups are used the cups are preferably longitudinally aligned and could be all or a combination of the different types of cups. Alternatively, where the plurality of cups are used if a wider toothbrush head is used the cups need not be longitudinally aligned. Although the sets of cups and bristle rings are illustrated as being uniformly spaced from each other, a non-uniform spacing could be used.

What is claimed is:

1. A toothbrush, comprising:
a head including a plurality of cleaning elements: the plurality of cleaning elements including at least two sets of cleaning elements generally aligned on an axis of the head, each set of cleaning elements having:
a closed ring of bristles formed about a center point, the ring of bristles spaced from and surrounding a central cleaning element located at the center point of the closed ring;
the central cleaning element being a circular cluster of densely packed bristles having a free end that is contoured to define a cup-shaped area; and
wherein the central cleaning element and the closed ring are spaced from one another to form a holding area enclosed within the closed ring; and
wherein the holding and cup-shaped areas are for retention of an oral care substance to be applied to the plurality of cleaning elements;
wherein at least one of the closed ring of bristles and the central cleaning element is mounted on a platform having a base with a slot formed in the underside thereof, the slot having sides, the toothbrush further comprising a drive shaft having an axis, the drive shaft further having an offset positioned within the slot such that when the drive shaft is oscillated about its axis the offset engages the sides of the slot to impart an oscillatory motion to the platform.

2. The toothbrush of claim 1, wherein additional cleaning elements are arranged on a periphery of the head.

3. The toothbrush of claim 2, wherein the additional cleaning elements are formed generally concentric with the central cleaning element and the closed ring.

4. The toothbrush of claim 1, wherein the central cleaning element and the closed ring each form a cleaning surface parallel with the face of the head, respectively: and wherein the cleaning surface of the closed ring extends farther from the head than the cleaning surface of the central cleaning element.

5. The toothbrush of claim 1, further comprising a plurality of sets of bristles at a distal end of the head and a plurality of sets of bristles at a proximal end of the head.

6. The toothbrush of claim 1, further comprising a first set of cleaning elements projecting from a distal end of the face of the head and a second set of cleaning elements projecting from a proximal end of the face of the head.

7. The toothbrush of claim 1, wherein the head comprises a plurality of closed rings of bristles and a plurality of central cleaning elements, each of the plurality of central cleaning elements comprising a circular cluster of densely packed bristles having a free end contoured to define a cup-shaped area, wherein each of the plurality of closed rings of bristles surrounds a respective central cleaning element;
wherein the toothbrush further comprises a plurality of platforms, each of the platforms having a base with a slot formed in the underside thereof, each of the platforms further having one of the closed ring of bristles and the central cleaning element mounted thereto;
wherein the toothbrush further comprises the drive shaft having a plurality of offsets spaced along a length of the drive shaft, one of the plurality of offsets positioned within a respective slot of one of the plurality of platforms; and
wherein when the drive shaft is oscillated about its axis the offsets engage the bases to impart an oscillatory motion to the platforms.

8. The toothbrush of claim 1, wherein the central cleaning element is mounted on the platform and the closed ring of bristles is not mounted on the platform such that when the drive shaft is oscillated about its axis the central cleaning element oscillates and the closed ring of bristles remains stationary.

9. A toothbrush, comprising:
a head including a plurality of cleaning elements extending from a face of the head: the plurality of cleaning elements including;
a central cleaning element of densely packed bristles having a free end that forms a cup-shaped area;
a closed ring of bristles spaced from and surrounding the central cleaning element, the central cleaning element located at a center point of the closed ring; and
wherein the central cleaning element and the surrounding closed ring are generally aligned along a central longitudinal axis of the head;
wherein at least one of the closed ring of bristles and the central cleaning element is mounted on a platform having a base with a slot formed in the underside thereof, the slot having sides, the toothbrush further comprising a drive shaft having an axis, the drive shaft further having an offset positioned within the slot such that when the drive shaft is oscillated about its axis the offset engages the sides of the slot to impart an oscillatory motion to the platform.

10. The toothbrush of claim 9, wherein the central cleaning element and the closed ring each define a respective contact surface spaced from the head, and wherein the contact surfaces of the central cleaning element and the closed ring extend substantially parallel to the head and define a holding area in conjunction with the spacing between the central cleaning element and the closed ring.

11. The toothbrush of claim 9, wherein the central cleaning element is a circular cluster of densely packed bristles.

12. The toothbrush of claim 9, wherein the head comprises a plurality of closed rings of bristles and a plurality of central cleaning elements, each of the plurality of central cleaning elements comprising a circular cluster of densely packed bristles having a free end contoured to define a cup-shaped area, wherein each of the plurality of closed rings of bristles surrounds a respective central cleaning element;
wherein the toothbrush further comprises a plurality of platforms, each of the platforms having a base with a slot formed in the underside thereof, each of the platforms further having one of the closed ring of bristles and the central cleaning element mounted thereto;
wherein the toothbrush further comprises the drive shaft having a plurality of offsets spaced along a length of the drive shaft, one of the plurality of offsets positioned within a respective slot of one of the plurality of platforms; and
wherein when the drive shaft is oscillated about its axis the offsets engage the bases to impart an oscillatory motion to the platforms.

13. The toothbrush of claim 9, wherein the central cleaning element is mounted on the platform and the closed ring of bristles is not mounted on the platform such that when the drive shaft is oscillated about its axis the central cleaning element oscillates and the closed ring of bristles remains stationary.

14. A toothbrush, comprising:
a head including a plurality of cleaning elements projecting from a face of the head, the plurality of cleaning elements including:
a central cleaning element of densely packed bristles having a free end that defines a cup-shaped holding area; and
a closed ring of bristles spaced from and confining the central cleaning element, the central cleaning element located at a center point of the closed ring:
wherein the central cleaning element and the closed ring are generally aligned on an axis of the head; and
wherein the central cleaning element, the closed ring and the relative spacing between the central cleaning element and the closed ring are configured to promote retention of an oral care substance within the closed ring when the plurality of cleaning elements are rotated or oscillated about an axis perpendicular to the face of the head;
wherein at least one of the closed ring of bristles and the central cleaning element is mounted on a platform having a base with a slot formed in the underside thereof, the slot having sides, the toothbrush further comprising a drive shaft having an axis, the drive shaft further having an offset positioned within the slot such that when the drive shaft is oscillated about its axis the offset engages the sides of the slot to impart an oscillatory motion to the platform.

15. The toothbrush of claim 14, wherein the plurality of cleaning elements are attached to a platform, the platform being configured to be rotated or oscillated by a power drive mechanism.

16. The toothbrush of claim 14, wherein the central cleaning element is a circular cluster of densely packed bristles.

17. The toothbrush of claim 14, further comprising an additional set of cleaning elements formed generally concentric with the central cleaning element and the closed ring.

18. The toothbrush of claim 14, wherein the head comprises a plurality of closed rings of bristles and a plurality of central cleaning elements, each of the plurality of central cleaning elements comprising a circular cluster of densely packed bristles having a free end contoured to define a cup-shaped area, wherein each of the plurality of closed rings of bristles surrounds a respective central cleaning element;

wherein the toothbrush further comprises a plurality of platforms, each of the platforms having a base with a slot formed in the underside thereof, each of the platforms further having one of the closed ring of bristles and the central cleaning element mounted thereto;

wherein the toothbrush further comprises the drive shaft having a plurality of offsets spaced along a length of the drive shaft, one of the plurality of offsets positioned within a respective slot of one of the plurality of platforms; and wherein when the drive shaft is oscillated about its axis the offsets engage the bases to impart an oscillatory motion to the platforms.

19. The toothbrush of claim 14, wherein the central cleaning element is mounted on the platform and the closed ring of bristles is not mounted on the platform such that when the drive shaft is oscillated about its axis the central cleaning element oscillates and the closed ring of bristles remains stationary.

* * * * *